United States Patent [19]

Reinhard

[11] Patent Number: 5,660,831

[45] Date of Patent: Aug. 26, 1997

[54] **EXTRACT FROM FLOWERS OF *SALVIA OFFICINALIS*, PROCESS OF ITS PREPARATION AND USE THEREOF**

[75] Inventor: Max Reinhard, Bad Homburg, Germany

[73] Assignee: Heilmittelbetrieb Isernhagen GmbH, Isernhagen, Germany

[21] Appl. No.: 495,481

[22] PCT Filed: Feb. 3, 1994

[86] PCT No.: PCT/EP94/00315

§ 371 Date: Jul. 24, 1995

§ 102(e) Date: Jul. 24, 1995

[87] PCT Pub. No.: WO94/17814

PCT Pub. Date: Aug. 18, 1994

[30] Foreign Application Priority Data

Feb. 10, 1993 [DE] Germany ............... 43 03 823.9

[51] Int. Cl.⁶ .................................................. A61K 35/78
[52] U.S. Cl. ........................................ 424/175.1; 514/821
[58] Field of Search ..................... 424/195.1; 514/821

[56] References Cited

U.S. PATENT DOCUMENTS 4,942,033  7/1990  Aubert et al. ................... 424/195.1

FOREIGN PATENT DOCUMENTS 0 147 331 A2  12/1984  European Pat. Off. .
0 454 097 A1  10/1991  European Pat. Off. .
WO88/02260   4/1988   WIPO .

OTHER PUBLICATIONS

*Hagers Handbuch Der Pharmazeutischen Praxis*; Complete Fourth Edition; P.H. List and L. Hörhammer; Springer-Verlag 1979.

"Chemieprodukte, Haushalt, Gewerbe, Industrie"; *Seifen-Öle-Fette-Wachse*; 116. Jg.; No. 16; 16 Oct. 1990.

Technologie Pflanzlicher Arzneizubereitungen; Prof. Dr. Dr. h. c. P. H. List and Prof. Dr. Peter C. Schmidt; 1984.

*Chemical Abstract*; vol. 103, 1985; p. 404; 103: 193127y.

*Chemical Abstract*; vol. 86, 1077; p. 250; 86: 117603r.

*17–Food, Feed Chem.*; vol. 114, 1991; p. 591; 114: 80195c.

*Primary Examiner*—John W. Rollins
*Attorney, Agent, or Firm*—Griffin Butler Whisenhunt & Kurtossy

[57] ABSTRACT

A method is described for obtaining an extract from the flowers of *Salvia officinalis*. The extraction process is performed preferably at a temperature of less than 50° C. A preferred extraction agent is supercritical $CO_2$. The extract thus obtained can be processed, if desired, with the addition of suitable thinners or fillers, in order to obtain a medicament. Medicaments containing the extract of *Salvia officinalis* flowers can be used to control high blood-pressure, circulatory problems and incomplete cicatrization of wounds.

13 Claims, No Drawings

EXTRACT FROM FLOWERS OF SALVIA OFFICINALIS, PROCESS OF ITS PREPARATION AND USE THEREOF

The invention relates to an extract of flowers of *Salvia officinalis* (sage) and a method of producing same. Furthermore, the invention relates to a medicament having a content of extract from flowers of *Salvia officinalis* and the use thereof in combating circulatory disorders and high blood pressure as well as in improving the healing of wounds.

High blood pressure and related cardiovascular diseases, which are not seldomly fatal, represent one of the major problems in medicine. Circulatory disorders are also often associated with serious complications. The problem of inadequate healing of wounds exists particularly with elderly people, so that wounds fail to heal in many cases even after a lengthy period.

Although intensive efforts have been made to develop synthetic drugs or natural remedies which are effective in the case of the aforementioned indications, there is ultimately still a continuous need for new medicaments, last but not least due to the side-effects which occur repeatedly.

In addition, the developed preparations are as a rule applicable only for one of the stated indications. In particular, effective means have yet to become known which are shown to be effective both in promoting circulation and in reducing blood pressure.

The use of plant extracts as natural remedies is known from ancient times. However, the extracts obtained from various types of plants, various parts thereof or under various conditions by extraction often differ basically in their effect.

From the sage plant the use of aqueous solutions having constituents from the leaves is known to counteract excessive perspiration, catarrhs and as medications for flushing and gargling. Such solutions are obtained e.g. by treating the sage leaves with hot water. Conventional methods of obtaining sage extracts include, apart from the actual extraction stage, e.g. including the use of alcohol, a stage of distilling off the extraction vehicle at temperatures above 100° C., many constituents being thermally damaged or changed thereby.

One object of the invention is to provide a method by which a novel extract having valuable constituents can be obtained from the sage plant (*Salvia officinalis*) whilst in particular avoiding thermal decomposition of the constituents to a major extent where possible.

The gist of the invention consists of obtaining valuable extracts from flowers of sage by implementing extraction as gentle as possible so that the valuable constituents of the flowers enter the extract practically unchanged.

The subject matter of the invention is a method of producing an extract of *Salvia officinalis* characterized by the flowers of this plant being extracted. The extraction is done preferably at a temperature below 50° C. Furthermore, the invention relates to an extract of the flowers of *Salvia officinalis* obtained by the method according to the invention.

In addition, the invention has as subject matter a medicament which is characterized by a content of the extract from flowers of *Salvia officinalis*.

The extract obtained according to the invention is suitable for use in combating circulatory disorders and high blood pressure as well as disorders in the healing of wounds.

Extracting the flowers of *Salvia officinalis* can be done with the aid of any means of extraction such as water, organic solvents or supercritical $CO_2$. One example of an organic solvent is ethanol. As already mentioned, the temperature during extraction and any subsequent stage required for removing the extractant at least in part, e.g. by distillation, should be 50° C. or lower and preferably 40° C. and lower to prevent thermal impairment of the constituents of the flowers. This means that in distillative separation the pressure must be reduced to the extent that the stated upper temperature limit can be maintained.

According to the invention the use of supercritical $CO_2$ for the extraction of sage flowers is particularly preferred since it can be carried out at low temperatures and thus particularly gently.

The extraction with supercritical $CO_2$ may be done in any apparatus suitable therefor. From the thermodynamic properties of $CO_2$, namely a critical temperature of 31.3° C. and a critical pressure of 71.5 bar, the lower limits for the temperature and for the pressure result for the extraction.

In particular, working at a temperature of 40° C. or below is preferred for extraction with $CO_2$, the pressure being preferably in the range from 90 to 300 bar.

Extraction may be continued until all constituents extractable with supercritical $CO_2$ have been extracted from the flowers of *Salvia officinalis*. This is usually the case after a 1 to 2 hour duration of the extraction method. However, according to the invention it is also possible to extract only part of the constituents from the flowers of *Salvia officinalis*.

One advantage in using supercritical $CO_2$ as the extractant as compared to the use of other extractants, such as ethanol or water, is that extraction can be done at temperatures below 40° C., whilst e.g. conventional alcoholic extraction requires the ethanol to be distilled off at temperatures of more than 100° C.

A further advantage of extracting with supercritical $CO_2$ is that solventless extracts may be obtained, thus avoiding any possible unfavorable influencing of the healing effect of the extract by such solvents as ethanol.

The extract according to the invention is preferably obtained from flowers of *Salvia officinalis*, other kinds of sage featuring constituents which differ substantially in part. In the same way a different composition of the extract is obtained from extracting other parts of the *Salvia officinalis* plant, such as roots, leaves or stalks.

After harvesting, the flowers of *Salvia officinalis* employed are preferably dried, i.e. at a temperature of 40° C. or below. Like the extraction temperature the drying temperature is maintained low to permit gentle treatment of the sage flowers. Also feasible is the employment of deep-frozen flowers.

The extract from flowers of *Salvia officinalis* obtained by the method according to the invention is pasty in consistency. This extract may be employed as an effective constituent of a medicament.

The medicament according to the invention may be produced in any presentation, the extract from flowers of *Salvia officinalis* being aggregated for this purpose with any suitable thinner, filler and the like before being transformed into the desired presentation. No special restrictions exist as regards the ratio of extract to thinner, filler and the like. Producing the medicament may be done according to usual pharmaceutical practice.

For internal application the medicament according to the invention may be administered orally, e.g. in the form of a tablet, a lozenge, a capsule, a powder, an elixier, a syrup and the like, or parenteral as an injection preparation. For producing a tablet the extract obtained by $CO_2$ extraction is mixed with a usual tablet filler such as lactose, the mixture then being compressed into tablets.

The medicament according to the invention may also be applied externally, e.g. in the form of an ointment, a cream or a tincture. To produce an ointment the $CO_2$ extract is mixed with an ointment base such as a fatty ointment base, one example of a fatty ointment base being Vaseline.

The medicament according to the invention has the effect of regulating, more particularly reducing, blood pressure. Accordingly, it may be employed e.g. in the form of tablets for the purpose of combating high blood pressure. The medicament according to the invention may also be employed to promote circulation. Accordingly, it may be used in the form of an ointment for the purpose of combating circulatory disorders. In addition, the medicament according to the invention may also be used to promote the healing of wounds, it thus for example being possible to heal the wounds of elderly patients which do not permit healing by other means. Accordingly, the medicament according to the invention may be employed to combat insufficient healing of wounds.

The invention will now be explained in more detail by way of examples:

EXAMPLE 1

In this example, the production of a $CO_2$ total extract is described. For this purpose hand-picked, dried flowers of *Salvia officinalis* were extracted for 2 hours at a pressure of 300 bar (total extraction) and a temperature of 40° C. with $CO_2$, 623 g extract being obtained from 15.2 kg flowers of sage. This corresponds to an extract yield of 4.1%. The extract was obtained as a paste.

EXAMPLE 2

In this example, obtaining a $CO_2$ selective extract is described. The conditions for extraction involved an extraction time of 2 hours, a pressure of 90 bar (selective extraction) and a temperature of 40° C., 14 g extract being obtained from 1.7 kg flowers of sage. This corresponds to an extract yield of 0.8%. The extract was obtained as a paste.

EXAMPLE 3

The pasty extracts obtained according to examples 1 and 2 were mixed with powdered lactose. The mixtures were compressed in a usual tabletting press into tablets. The tablets contained 4 to 5 mg extract and were 9 mm in diameter and 3 mm thick.

EXAMPLE 4

The extract obtained by the method described in Examples 1 and 2 was mixed with Vaseline as the ointment base. The ointment contained 0.1% extract, relative to the ointment base.

EXAMPLE 5

In this example the effect in reducing blood pressure of tablets having a content of the extract according to the invention is described.

Following administration of one tablet (cf. Example 3) a day the blood pressure of a male patient 35 years of age dropped from 145 to 102, after 4 days from 123 to 95. In the case of another male patient 35 years of age the blood pressure dropped from 147 to 105, after 6 days from 121 to 88 on a daily dose of one tablet.

What is claimed is:

1. A method of treating circulatory disorders, high blood pressure and wound healing disorders, comprising administering to a human having circulatory disorders, high blood pressure or wound healing disorders, an effective amount of an extract from flowers of *Salvia officinalis*.

2. A method according to claim 1, wherein said extract is administered to a human having a circulatory disorder.

3. A method according to claim 1, wherein said extract is administered to a human having high blood pressure.

4. A method according to claim 1, wherein said extract is administered to a human having a wound healing disorder.

5. A method of treating circulatory disorders, high blood pressure and wound healing disorders, comprising administering to a human having circulatory disorders, high blood pressure or wound healing disorders, an effective amount of an extract from flowers of *Salvia officinalis* made by the steps of:

(a) providing flowers of *Salvia officinalis*; and
   (b) extracting the flowers of *Salvia officinalis* with supercritical CO2 at a temperature of 50° C. or below.

6. A method according to claim 5, wherein the step (b) is carried out at a pressure of between 90 and about 300 bar.

7. A method according to claim 6, wherein the step (b) is carried out at a temperature of 40° C. or below.

8. A method according to claim 7, wherein said flowers of *Salvia officinalis* have been dried at a temperature of 40° C. or below.

9. A method according to claim 5, wherein said step (b) is carried out for about two (2) hours at a pressure of about 90 bar.

10. A method according to claim 5, wherein said step (b) is carried out for about two (2) hours at a pressure of about 300 bar.

11. A method according to claim 5, wherein said extract is administered to a human having a circulatory disorder.

12. A method according to claim 5, wherein said extract is administered to a human having high blood pressure.

13. A method according to claim 5, wherein said extract is administered to a human having a wound healing disorder.

* * * * *